United States Patent [19]

Shaw

[11] 4,059,988
[45] Nov. 29, 1977

[54] PRELIMINARY SCREENING OF WOODEN POLES

[75] Inventor: Alan Douglas Shaw, Geilston Bay, Australia

[73] Assignee: Fanner Pty. Limited, Northmead, Australia; a part interest

[21] Appl. No.: 689,434

[22] Filed: May 24, 1976

[30] Foreign Application Priority Data

June 5, 1975 Australia .............................. 1891/75

[51] Int. Cl.² ...................... G01N 29/00; G01M 7/00
[52] U.S. Cl. .................................................... 73/579
[58] Field of Search .................. 73/67.5 R, 67.2, 67.1, 73/67.6, 556, 559, 561

[56] References Cited

U.S. PATENT DOCUMENTS

| | | | |
|---|---|---|---|
| 3,066,525 | 12/1962 | Harris ............................... | 73/67.5 R |
| 3,345,861 | 10/1967 | Heath .................................... | 73/67.2 |
| 3,531,983 | 10/1970 | Heath et al. ......................... | 73/67.2 |
| 3,877,294 | 4/1975 | Shaw .................................... | 73/67.2 |

Primary Examiner—Richard C. Queisser
Assistant Examiner—Anthony V. Ciarlante
Attorney, Agent, or Firm—Ladas, Parry, Von Gehr, Goldsmith & Deschamps

[57] ABSTRACT

A method and apparatus for screening wood poles to identify those in which rot or other deterioration has occurred to an extent which justifies a more detailed examination, comprises injecting "white sound" into the pole at 40Hz and measuring the amplitudes of vibrational energy at 100Hz and 350Hz opposite the point of injection. A comparison of the amplitudes of these frequencies is used to signify whether the pole has passed the screening. Two such tests are conducted at perpendicular positions on the pole. The screening apparatus may be combined with apparatus for conducting a more detailed examination of the pole if it fails to pass the screening test.

15 Claims, 5 Drawing Figures

PRELIMINARY SCREENING OF WOODEN POLES

FIELD OF THE INVENTION

This invention relates to the non-destructive testing of wooden poles and like objects to sort out those which are sound from those whose characteristics, when tested, indicate that they may have deteriorated. A subsequent, more searching test can then be confined to the poles which have possibly deteriorated so that time is not wasted conducting searching tests on sound poles. The invention is particularly, although not exclusively, applicable to hardwood poles used to carry overhead transmission lines to remote areas of the country.

STATE OF THE ART

The presence of voids, rotten areas and severe internal splits within a wooden pole are usually not apparent from a visual examination of its surface. Taking samples by boring is unsatisfactory because it is now recognised that this promotes deterioration. Other techniques which are non-destructive have therefore been devised. Field work in the U.S.A. has indicated that techniques using x-rays are usable and similar work in Australia involving field trials has shown that techniques using sound waves are equally usable and have the advantage that they require less sophisticated equipment.

The X-ray equipment for carrying out an X-ray examination of an upright wooden pole carrying an overhead line, is expensive and pole testing by this technique is relatively slow. The technique using sound waves is quicker in that a pole can be examined in 15 minutes. One example of this technique is described in the Applicants' U.S. Pat. No. 3,877,294. In this specification is described the use of vibration head to inject a sound signal into the pole at a predetermined point. The signal has a frequency at which the pole is found to display certain resonant characteristics. The vibrational energy at different listening points along the pole and on the opposite side to the point of injection, is then detected by an electro-mechanical transducer. A comparison is made between the emergent energy at a reference listening point directly opposite the injection point, and the emergent energy at other listening points and the presence of voids or regions of rot in the pole is detected by the emergent energy level at the reference listening point being less than that at one of the other listening points. The basic theory underlying sound wave examination of wood is not clearly understood. One theory suggests that high sonic frequencies are transmitted through good woods more easily than low frequencies, i.e., good wood presents a lower acoustic impedance to high frequencies than to low frequencies. However, if the texture of the wood changes, as a result of rot or voids, the acoustic impedance increases at high frequencies and diminishes at low frequencies. The lower frequencies of the sound injected are then conducted more easily than the high frequencies and the increase in low frequency radiated sound is detected at the corresponding listening point. A different theory suggests that a pole containing a split, void or rotten region, behaves rather like an open-ended organ pipe and the relative intensities of different sound frequencies radiated from it is a function of the dimensions of the split, void or rotten region.

The fact that sound wood has a different acoustic response frequency to unsound wood has been used in equipment developed for preliminary screening of wooden poles before subjecting them to X-ray examination. The advantage of preliminary screening is that normally only a few percent of timber poles carrying overhead power lines exhibit characteristics signifying that they should be subjected to a more searching examination. As examination using X-ray techniques is time-consuming and expensive, the practical advantage of preliminary screening of the poles from the point of view of time-saving is considerable. Such preliminary screening equipment is described in U.S. Pat. No. 3,531,983. A pole to be screened is struck repeatedly with a hammer to inject "white" sound into it, i.e., sound covering a complete range of sonic frequencies, and an electro-magnetic transducer is used to provide an electrical output significant of the energy levels at all frequencies on the side of the pole opposite the point hammered. Two filters, one having a low frequency band pass of about 160Hz to 600Hz and the other having a high frequency band pass of about 1000Hz to 5200Hz are connected in parallel to receive the output of the transducer. The electrical outputs of the filters which signify the magnitudes of the energy received by the transducer in in the two frequency ranges, are fed, in opposition, to a meter. The direction and magnitude of the deflection of the meter from a centre position denotes the comparative magnitude of low frequency signals with respect to the high frequency signals. The greater the magnitude of the low frequency signals, the greater is the likelihood of the post being sub-standard as such signals are attenuated less by rotten wood then by sound wood. In practice, screening a wooden pole by this technique involves three readings at axially spaced positions on the pole and although the time taken is substantially less than for an X-ray investigation, it would not seem to be less than the time taken to do a thorough check by the acoustic method described in U.S. Pat. No. 3,877,294.

OBJECT OF THE INVENTION

An object of the invention is the provision of an improved method and apparatus for preliminary screening wooden poles to separate poles of acceptable quality from those whose characteristics appear from the test to indicate that the pole may be sub-standard.

THE INVENTION

A method of preliminary screening a wooden pole to see if its characteristics are such that a more thorough examination is called for, comprises injecting into the pole at a first position a mechanical signal of constant amplitude and at a chosen constant frequency; connecting to a listening point on the other side of the pole an electro-mechanical transducer providing an electrical output significant of the level of mechanical vibratory energy present at the listening point; passing the electrical output through two filters having mutually exclusive pass bands the first filter passing a frequency or range of frequencies found empirically to be virtually unaffected by the condition of the pole and the second filter passing a frequency or range of frequencies whose amplitude is found empirically to be significantly affected by the condition of the pole; comparing the levels of the electrical outputs of the two filters with one another; and providing a read-out value obtained from the comparison and which signifies with its magnitude whether the pole should be examined more thoroughly. Preferably the method of the invention is performed twice on each pole at two positions respectively displaced from one another 90° around the circumference of the pole.

The electrical outputs of the two filters may be obtained simultaneously or sequentially. The method of the invention may be utilised in apparatus designed for carrying out pole scanning alone, or it may be used in conjunction with testing apparatus described in our U.S. Pat. No. 3,877,294 so that a linesman can, with a single unit, conduct a pole screening operation followed by a more detailed examination of "suspect" poles found as a result of the screening.

The invention also includes apparatus for carrying out the above method such apparatus comprising a vibrator for injecting into the pile a mechanical signal, an electrical circuit for determining the frequency of operation of the vibrator and the amplitude of signal, an electro-magnetic transducer for providing an electrical output significant of the frequencies and amplitudes of vibratory energy present at a listening point at which the transducer is located on the pole when the apparatus is in use, analysing circuitry connected to receive the electrical output of the transducer and to supply a read-out value significant of the pole's condition, two mutually exclusive band-pass filters in the circuitry arranged to receive the electrical output of the transducer one of the filters passing a first frequency or range of frequencies whose attenuation is found empirically to be unaffected by the condition of the pole, and the other filter passing a frequency or a range of frequencies whose attenuation is found to be significantly affected by the condition of the pole, circuit means in said circuitry and which receives the electrical outputs of the two filters, and a read-out device in the circuitry to give a comparative reading of the electrical outputs of the two filters.

PREFERRED FEATURES OF THE INVENTION

Work done on hard-wood poles carrying transmission lines in Tasmania has shown that if the first filter has a narrow band-pass peaking at about 100Hz and the second filter has a narrow band-pass peaking at about 350Hz, excellent results are achieved when the repetition frequency of the signal injected into the wood is 40Hz. From an intensive examination of a large number of poles it appears that signals having a frequency of about 100Hz are attenuated to a negligible extent by the condition of the wood through which they pass. On the other hand, signal frequencies at about 350Hz are greatly influenced by the condition of the pole and are very much less attenuated when the pole contains splits, voids or rot than when the pole is in good condition. This is a surprising result because, as is clear from U.S. Pat. No. 3,531,983 it has always been assumed that one could only get meaningful information about the condition of a pole from a wide pass-band filter operating beneath 600Hz if one compared the level of its output with that of a second wide pass-band filter operating between 1000Hz and 6000Hz. It has never previously been suspected that, within the lower of these two pass bands, there are individual frequencies or narrow frequency ranges which enable the pole condition to be evaluated without recourse to the higher frequency pass-band. Moreover, it appears that the screening technique of the invention is independent of the position of a void or rotten area in the wood so that in carrying out the invention in its broadest form, a single listening point in each pole provides all the information required.

It should be observed that, unlike the technique described in our U.S. Pat. No. 3,877,294, no attempt is made to tune the injection frequency to provide a resonant effect with the pole. For screening purposes a single low repetition frequency of for example, 40Hz, is injected into the pole, with preferably a maximum amplitude.

Conveniently the apparatus described in U.S. Pat. No. 3,877,294 is provided with controls enabling it also to be also used for screening purposes, as is described below, as well as for pole testing.

The invention will now be described in more detail, by way of example, with reference to the accompanying drawings in which:

PREFERRED EMBODIMENT

In the accompanying drawings corresponding parts have like reference numerals.

Figure 1:
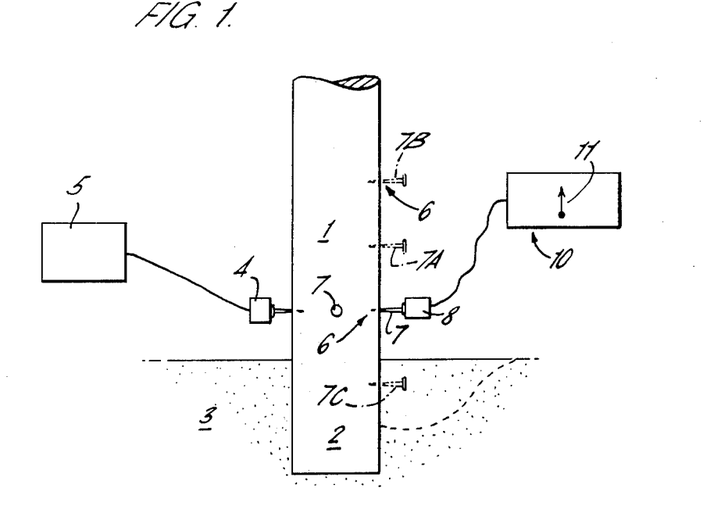
FIG. 1 shows a section of a wooden pole being preliminarily screened to see if its characteristics indicate it to be possibly sub-standard.

FIG. 1 shows an upright wooden pole 1 having its lower end 2 buried in the ground 3, being subjected to preliminary screening. This is effected by injecting vibrational energy into the pole 1 with a mechanical vibrator 4 operated at a predetermined frequency determined by a frequency controller 5 and which subjects the pole to a stream of impacts of the same magnitude. In practice, the preferred predetermined impact repetition frequency is 40 impacts per second.

A listening point 6 is formed in the pole approximately diametrically opposite the vibrator 4 by driving into it a spike 7. An electro-magnetic transducer 8 is clamped to the protruding end portion of the spike 7 and electrical signals from it are fed to analysing equipment 10 provided with a meter 11 to enable the user of the apparatus to read at a glance whether the pole is in good condition or is "suspect". In practice, the vibrator 4, controller 5, transducer 8, equipment 10 together with leads and an assortment of spikes 7 are mounted in an instrument case which is readily carried by the user of the apparatus. The assemblage provides a modified version of the RESOTEST pole checking apparatus marketed by Fanner Pty., Ltd., of Australia and described in detail in their United States Pat. No. 3,877,294 hereby inserted by way of reference.

Figure 2:
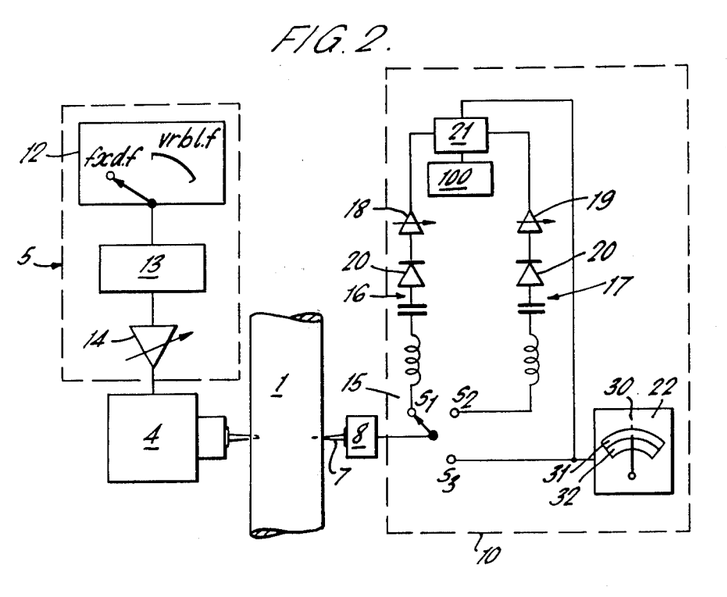
FIG. 2 is a simplified electrical block diagram of equipment used for carrying out the screening and also, if necessary a more thorough examination of the pole.

Referring to FIG. 2, the frequency controller 5 contains a two position switch 12. One position is fixed and is marked "fxd.f" and the other position is adjustable and is marked "vrbl.f". The position of the switch 12 determines the frequency of the impacts applied to the pole by the vibrator 4. When in the position shown, used for screening, the frequency of impacts is fixed at 40Hz. If the apparatus is to be used for a thorough investigation of a particular pole, found by screening to be dubious, such an investigation is carried out as described in U.S. Pat. No. 3,877,294. The frequency of the impacts then has to be variable to obtain the frequency at which a resonance with the pole occurs. The switch 10 is moved to the adjustable "vrbl/f" position to enable this to be done. However this facility is not used during the screening procedure.

The switch 12 controls the frequency of a square wave oscillator 13 whose output is supplied through a variable amplifier 14 to the vibrator 4. For screening, the amplification of the amplifier is set to a maximum to inject the strongest signal into the pole.

The shock waves injected into the pole by the vibrator impacts produce a "white" spectrum of frequencies which are attenuated to different extents in the wood of the pole. The energy levels or amplitudes of these frequencies are transmitted through the spike 7 to the transducer 8 which produces corresponding electrical output signals fed to a selector switch 15.

The switch 15 has three positions and is shown in one of the two positions $S_1$, $S_2$ used for screening. The other position, $S_3$ is the pole testing (RESOTEST) position. The signals from the transducer 8 are supplied, in turn, to two narrow pass-band filters shown diagrammatically. and referenced 16 and 17 and connected to the switch positions $S_1$ and $S_2$ respectively. Signals transmitted through each of the two filters are first rectified at respective diodes 20 and then amplified and smoothed, to provide analoque values, by respective preset amplifier 18 and 19 before being fed to respective input terminals of a junction circuit 21. The junction circuit provides an electrical read-out value to a meter 22 from which the ratio of the magnitudes of the two comparator inputs can be obtained.

If switch 15 is moved to its third position $S_3$, the transducer 8 output is fed directly to the meter 22 as is required for a thorough investigation of the pole by the RESOTEST technique referred to earlier. The meter is an amplitude measuring device, such as a voltmeter. The filter circuit 16 is shown in detail in FIG. 5 and peaks at 100Hz with −3dB points at 105Hz and 95Hz. A tolerance of ±2Hz is permissible. The filter circuit 17 peaks at 350Hz with its flanking −3dB points at approximately 335Hz, and approximately 365Hz respectively with a tolerance of ±5%. The filters are narrow-band filters operating at relatively low frequencies, and having the same Q-factor of 12 although other values of Q lying between 8 and 16 give adequate results. The amplifiers 18 and 19 are in the ratio of 1:8. This ratio has been found empirically with a tolerance of ±5% to represent that which separates good poles from poles whose screening characteristics indicate that a more thorough examination of them is necessary.

The meter 22 has a mid-datum point 30 and its pointer moves over two scales 31, and 32. Scale 31 is used for screening and scale 32 for a thorough examination of the pole by the RESOTEST method. Scale 31 has its half to the left of the datum point 30 coloured green, signifiying the pole is free of voids and rot, and its half to the right coloured yellow, signifying the pole is suspect. It is also calibrated from 1 to 20, although this is not essential.

OPERATION OF PREFERRED EMBODIMENT

Figure 5:
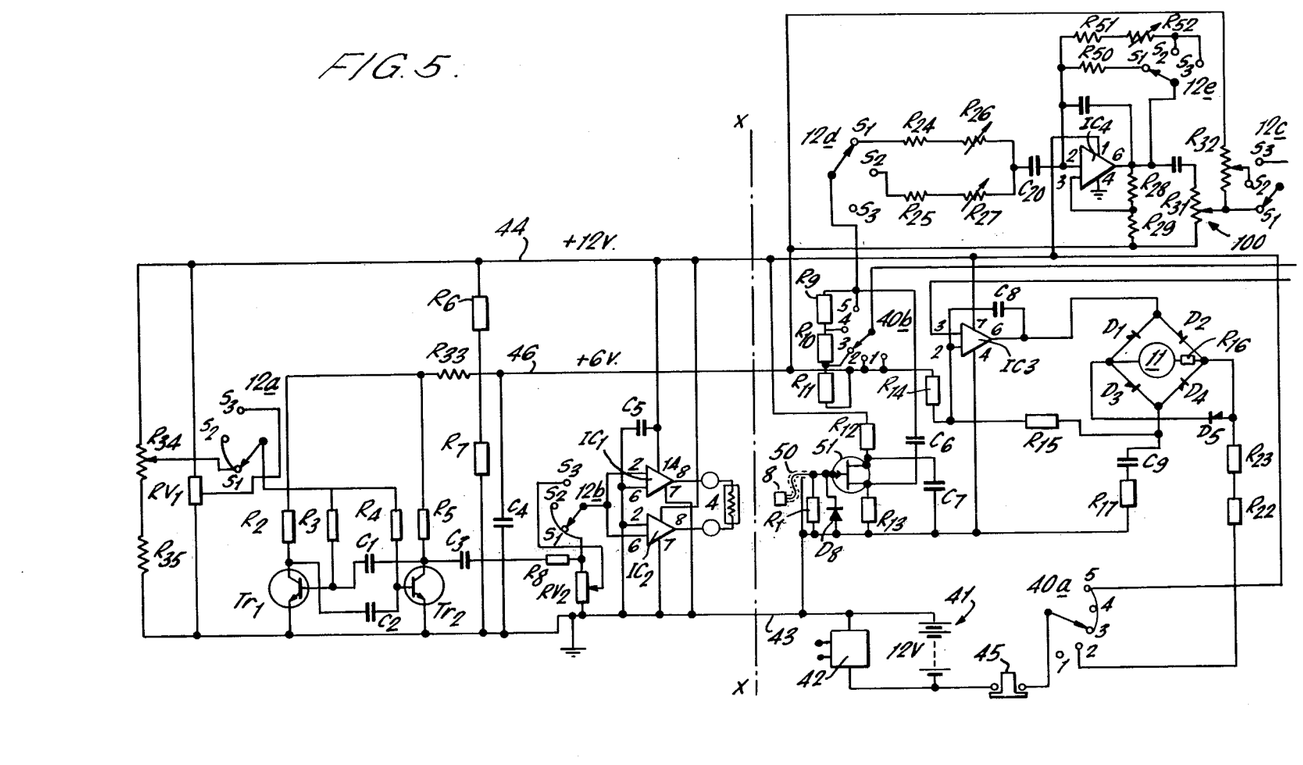

Four spikes 7 are partially driven into the pole about 125mm above ground level and at 90° to one another. If a full RESOTEST procedure is to be carried out — as described in U.S. Pat. No. 3,877,294 — these spikes will form part of the spike array used for that procedure. The vibrator 4 is then applied to one of the two pairs of diametrically opposite spikes and the other spike of the pair provides the spike 7 of FIG. 2. The switches 12 and 15 are placed in the positions shown in FIG. 2 and the equipment is switched on. A calibration control, referenced 100 in FIG. 5 is adjusted until the meter needle is in the datum position 30 marked on the dial of the meter 22. The switch 15 is then moved to position $S_2$ and the movement of the needle is observed. If it moves into the yellow half of the scale 31, it denotes that the wood is suspect. If it moves into the green half of the scale, the pole wood probably in good condition but, for completeness, a second similar procedure is performed on the other pair of spikes at right angles to the first pair. If, in both cases, the needle reading is in the green half of the scale, the pole has passed the screening. If the meter reads in the yellow half of the scale, the RESOTEST procedure is performed, as has already been described in U.S. Pat. No. 3,877,294, by applying spikes 7A, 7B and 7C in a vertical line with one of the two spike positions used in the screening test which gave the "yellow" scale reading, one of the spikes added being at the RESOTEST datum position 750 mm above ground and having a further spike driven into the diametrically opposite position on the pole for mounting the vibrator 4, the RESOTEST procedure is then carried out by moving the switch 12 to the "vrbl f" position and the switch 15 to the position $S_3$.

The presence of rot in the pole at the RESOTEST datum position can spoil the RESOTEST readings. However, in the case of a "yellow" scale reading of the screening test the condition of the pole at 750mm above ground level can be checked by augering out to 125mm and examining the wood chips for decay. If less than 25mm of rot or space exists at the end portion of the bore, it may be ignored. Neither the screening procedure or the RESOTEST procedure will give satisfactory results if the pole is visibly badly shattered or has gaping splits admitting daylight from one side to the other.

Practical experience has shown that poles can be screened very quickly by the above technique and that time is not wasted conducting a needless thorough examination of sound poles which, in practice, represent about 90% of the poles screened.

It has been found that of approximately 10% of the poles subjected to a subsequent searching examination as a result of being graded suspect in screening procedure 3% were found to be badly cracked but still serviceable and 7% were seriously decayed. Although, by reducing the ration of 1:8 to 1:5 the screening would separate the completely sound poles from the remainder, the ratio of 1:8 is preferred because poles do not become unserviceable through cracking alone unless the cracking is very severe. In the latter case, they are detected on a 1:8 ratio setting. If the ratio is increased to 1:9 it has been found that on rare occasions a rotten pole which ought to be replaced will pass through the preliminary screening. The ratio of 1:8 gives a "fail safe" margin which makes this ratio preferred.

EMPIRICAL WORK FROM WHICH THE INVENTION STEMS

Figure 3:
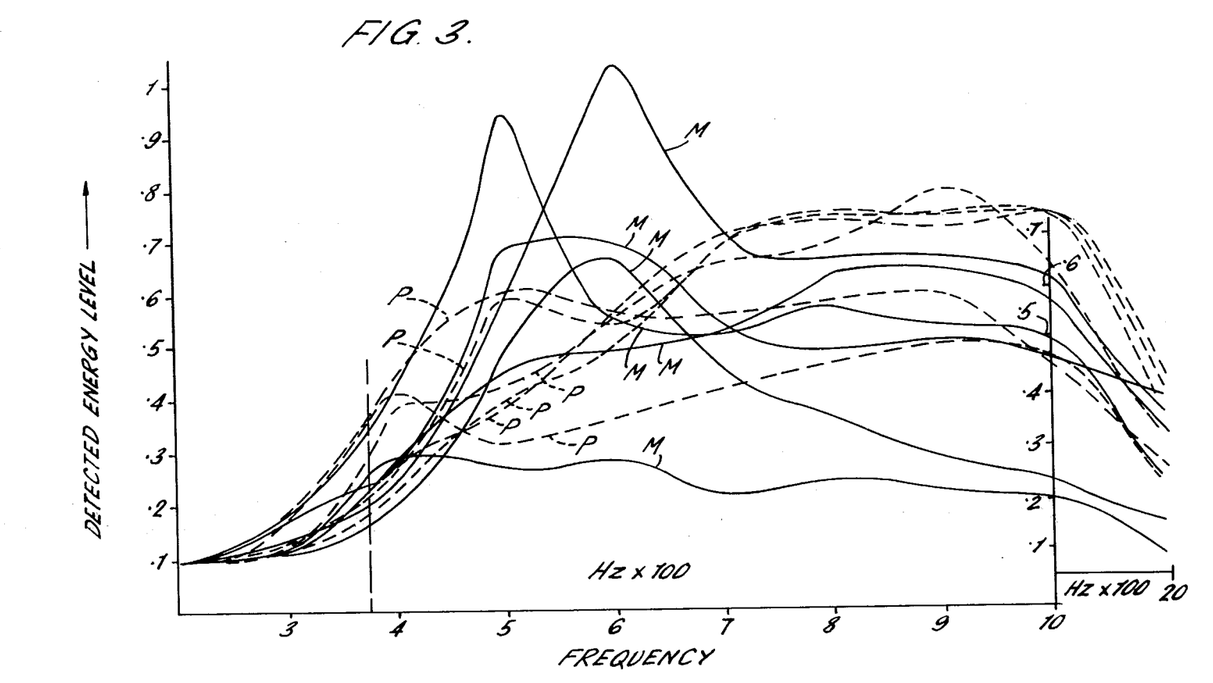
FIG. 3 shows graphically characteristic curves obtained at different points above ground on two wooden poles of slight different diameter and one of which is decayed, i.e., sub-standard, and the other of which is good, the curves being plots of the energy levels against frequencies between 200Hz and 2000Hz.

Tests conducted on a large number of poles by tapping them manually with a hammer and recording the detected energy levels at different frequencies and at different heights along the pole, showed that nothing of value can be ascertained because the curves of energy output at different frequencies are different at each listening point on the pole and also differed at the same listening point for consecutive hammer blows struck at the same injection point. However, when a hammer having a reproducible performance such as the vibrator of the RESOTEST system was used, traces of the shape shown in FIG. 3 were obtained and from a careful examination of hundreds of such traces certain conclusions were drawn FIG. 3 shows variations of the detected energy level with frequency at different listening points along the length of two poles. The continuous lines M showed frequency against energy-level curves for six axially spaced listening points in a decayed pole, and the broken lines P showed corresponding curves for a sound pole. These curves showed that, as expected, the energy levels at frequencies above 1000Hz for a sound pole were generally greater than for an unsound pole. However, the curves also showed, quite unexpectedly, that although in the zone from 400Hz to 1000Hz the curves are so interlaced as to provide no worthwhile information, there was a zone at between 300Hz and 400Hz in which the curves were more ordered. An examination of a large number of curves in the range of 300Hz to 400Hz for a large number of poles showed that the most meaningful information was obtained with the injection and listening points approximately diametrically opposite one another and at a distance not less than 100mm above ground level.

Figure 4:
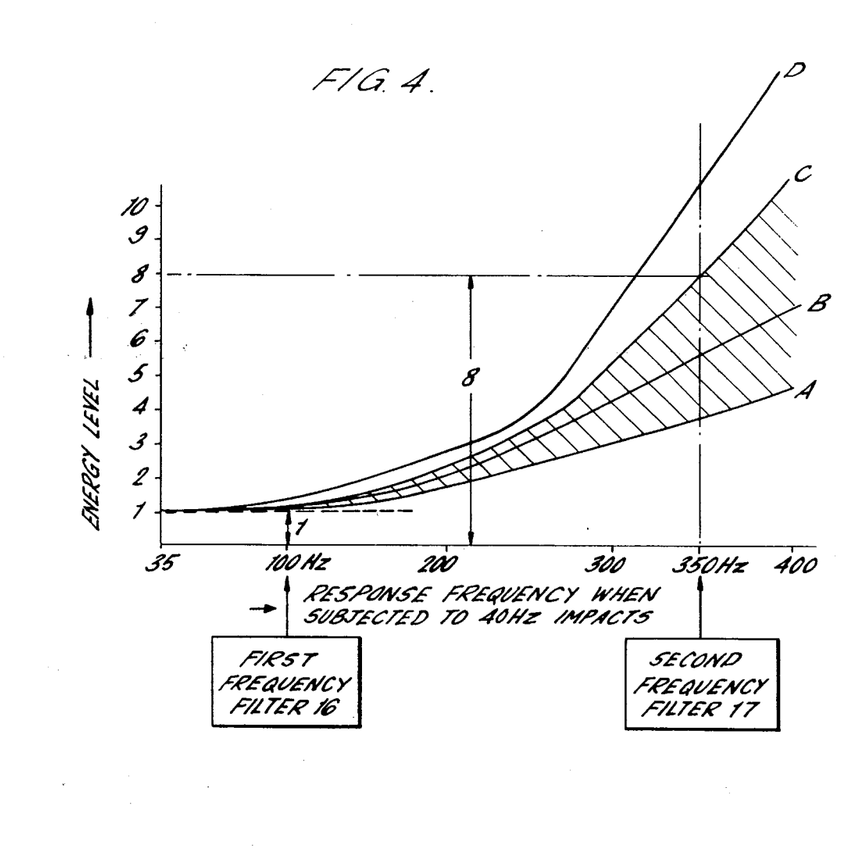
FIG. 4 shows graphically typical characteristic curves obtained from four typical poles of which three are in good condition, and shows the energy levels at a listening point the same distance above ground in each case, and at different frequencies in the range 35Hz to 400Hz; and, FIG. 5 shows a detailed electrical circuit diagram of the equipment of FIG. 2.

The hundreds of poles examined were then re-classified in accordance with their type and condition. Their curves of frequency against energy level between 35Hz and 400Hz were then plotted when subjected to 40 Hz frequency impacts by the vibrator 4 at 125 mm above ground level. The characteristic curves were found to fall into four distinct groups and a typical curve of each group is plotted in FIG. 4. Curve A in FIG. 4 is typical of a good quality untreated pole; curve B is typical of a good treated pole with acceptable cracking; curve C is typical of an untreated pole with acceptable cracking; and, curve D is that of an unacceptable pole. A large number of poles were used in this analysis and, surprisingly, it was found that irrespective of fluctuations in the diameters of the poles and their lengths, the pole characteristics roughly corresponded to one of the four curves A to D.

The shaded area between the curves C and A represents an envelope and all the acceptable poles examined had characteristics lying within it. Curves which extend outside the envelope for example curve D, represented poles in an unacceptable condition. The 1:8 ratio at 100Hz and 350Hz is apparent.

MODIFICATIONS TO PREFERRED EMBODIMENT

Changes in the above apparatus may be made. For example the operating frequency of the lower frequency filter is variable between 80Hz and 120Hz and 100Hz is simply the optimum value found in this range for hard woods. Similarly the upper frequency filter is variable between 275Hz and 400Hz with the optimum value for hard woods of 350Hz. With soft woods this frequency may be different. Finally, the impact repetition frequency of the vibrator may be chosen anywhere between 10Hz and 40Hz but it is important that it is so chosen that its simpler harmonics are well clear of the frequencies of operation of the filter circuits otherwise misleading results will be obtained. The preferred impact repetition frequency is 40Hz. It will be understood that the frequency values selected above, are those found empirically to be suitable for "hard" woods. Tests thus far have not been conducted on "soft" woods which may well respond to the same frequencies or ranges of frequencies. However, the selection of the best frequencies for screening soft woods can be found empirically by field testing as has been done for hard woods, as is explained above.

The circuit diagram of FIG. 5 will now be explained.

The electrical circuitry shown in FIG. 5 is energised by a 12-volt battery 41 connected in parallel to a battery charger 42 between an earth line 43 and a 12-volt line 44 which is energised by way of a push-button switch 45 and a 5-position selector switch 40 having two wafers 40a and 40b. Energisation of the line 44 occurs in any of positions 3-5 of the wafer switch 40. Position 2 of the switch 40 allows the meter 11 to be checked.

The voltage between the line 44 and 43 is divided by a potentiometer chain of resistors $R_6$ & $R_7$ to provide a 6-volt line 46. The circuitry shows a broken line X—X which denotes the split between the vibrator energisation circuit 5 and the analysing equipment 10.

The vibrator energisation circuit comprises a resistance chain $R_{34}$ & $R_{35}$ connected between the lines 44 and 43. A tapping is taken from the resistance $R_{34}$ to a switch position $S_1$ of the 3-position switch 12. Switch 12 has five banks, individually referenced with the letters a to e. The switch position $S_1$ of the switch bank 12a is connected to the switch position $S_2$ to provide a constant bias voltage to a square-wave oscillator circuit provided by a multi-vibrator provided by two emitter-follower transistors $Tr_1$ and $Tr_2$ Capacitors $C_1$ and $C_2$, and resistors $R_2$, $R_3$ and $R_5$. If the wiper of the switch bank 12a is move to position $S_3$, as is required for the RESOTEST procedure, the multi-vibrator oscillates at a different frequency determined by the setting of a potentiometer $RV_1$ connected between the lines 43 and 44. As shown, the multi-vibrator oscillates at 40Hz. The load resistors $R_2$, $R_5$, of the transistors of the oscillator are connected to the 6-volt line 46 through a resistance $R_{33}$. The square wave output of the oscillator circuit is fed through a capacitor $C_3$ to a resistor $R_8$ connected in series with a potentiometer $RV_2$ to earth. The junction of the resistor $R_8$ and potentiometer $RV_2$ is connected to the switch positions $S_1$ and $S_2$ of the second switch bank 12b and the tapping of the potentiometer $RV_2$ is connected to the third switch position $S_3$. The potentiometer $RV_2$ provides a gain control for a following push-pull amplifier stage. The voltage applied to the switch positions $S_2$ and $S_1$ of the switch bank 12b ensures that the amplifier gain is a maximum when the equipment is in its pole-scanning mode.

The wiper of the switch bank 12b is connected to a pair of integrated circuit power amplifiers $IC_1$, $IC_2$ which are connected as shown. They are each of type LM 380 (national semi-conductors) and their terminals are connected so that the amplifiers operate in push-pull. The capacitor $C_5$ acts as a de-coupler to stop the amplifiers from oscillating and is normally in the range 1-10 micro farads.

The push-pull output of the two amplifiers is fed to the vibrator 4 which has 15 ohms resistance and is constructed as a moving coil attached to an inertial mass as is used with currently available RESOTEST instruments made in accordance with the aforesaid U.S. Patent.

The piezo-electric transducer 8 is connected by a co-axial cable 50 to the input junction of a field effect transistor 51. This is connected as a source follower and is of type 2N5457-J. FET A resistor $R_1$ in parallel with a diode $D_8$ protects the transistor 51 from surge voltages at the input. The components $C_7$ and $R_{12}$ act as an AC de-coupling filter to prevent the risk of power supply ripple affecting the input to the following amplification stage.

The output of the transistor 51 is taken through the coupling capacitor $C_6$ to one end of a resistance chain formed by resistors $R_9$, $R_{10}$, and $R_{11}$. These are associated with the positions of a second bank 40b of the switch 40 which acts as a gain-control switch. The first two positions of the wiper of the switch bank 40b are connected to the 6-volt line 46; the junction of the resistors $R_{10}$ and $R_{11}$ is connected to the third position; the junction of the resistors $R_9$ and $R_{10}$ is connected to the fourth position; and the fifth position of the switch is connected between the capacitor $C_6$ and the resistor $R_9$ and also to a switch bank 12d which is shown in the first pole-scan position at which it is connected to the filter 16 shown in FIG. 2. The wiper of the switch bank 40b is connected to a switch position $S_3$ of a further switch bank 12c of the switch 12.

The switch bank 12d has two effective switch positions $S_1$ and $S_2$. The first switch position $S_1$ is connected through resistors $R_{24}$ and $R_{26}$, which is adjustable, to control the Q-factor of the filter circuit. The second switch position $S_2$ of the switch bank 12d is connected through resistors $R_{25}$ and $R_{27}$, which is also adjustable, to vary the Q-factor of the second filter circuit. The signal obtained from the two switch positions $S_1$ and $S_2$ are fed through a capacitor $C_{20}$ to the input of a Wien bridge filter circuit provided by a "741" integrated circuit operational amplifier $IC_4$ connected as shown. This configuration of amplifier is well known in the art and requires no further explanation. The output from the amplifier $IC_4$ is obtained at a terminal 6 and is developed across a load potentiometer $R_{31}$. The resistors $R_{28}$ and $R_{29}$ provide feedback to terminal 3 of the amplifier, and the response frequency of the filter circuit is determined by the position of the wiper of a further switch bank 12e, which is connected to the output terminal of the amplifier and has three positions. At its first switch position $S_1$, corresponding to the 100Hz filter position, a resistor $R_{50}$ of 100kilohms is introduced into a second feed-back circuit of the amplifier $IC_4$ in order to provide it with a response frequency of 100Hz. At the second switch position $S_2$, the resistor $R_{50}$ is replaced by two series connector resistors $R_{51}$ and $R_{52}$ of 27 kilohms and 5 kilohms (adjustable) respectively, which change the pass-band of the filter amplifier $IC_4$ from 100Hz to 350Hz.

The wiper of the load potentiometer $R_{31}$ of the amplifier $IC_4$ is connected to the switch position $S_1$ of the switch bank 12c to provide a calibration potentiometer. It is also connected to a potentiometer $R_{32}$ which has its other end connected to the 6-volt line 46 and its wiper connected to the position $S_2$ of the switch-back 12c.

The wiper of the switch bank 12c is connected to the input side of an integrated circuit amplifier $IC_3$ which is also of the 741 type and is connected as shown. This provides an alternating output voltage which is applied across a bridge rectifier formed by the four diodes $D_1$ to $D_4$ and which has the meter 11 connected across its direct current terminals. These are also connected, in one case by the diode $D_5$, to a resistance chain formed by resistors $R_{22}$ and $R_{23}$, to the second or meter-test position of the gain switch 40.

To place the circuitory of FIG. 5 into its pole-scanning mode the switch 12 is placed in its $S_1$ position. It will be appreciated that the switch 15 of FIG. 2 is in fact provided by the banks of switch 12. In both of the positions $S_1$ and $S_2$, the multi-vibrator oscillates with a repetition frequency of 40Hz and the switch bank 12b ensures that the push-pull amplifier of the vibrator 4 has maximum amplitude of output.

Signals picked up by the transducer 8 are fed through the switch bank 12d to the filter which operates to allow 100Hz signals through it by virtue of the switch bank 12e. The signals are applied to the calibration potentiometer $R_{31}$ which is manually controlled so that its output, which is fed through the switch bank 12c, causes the meter 11 to assume the predetermined datum position 30 shown in FIG. 2. The gain control switch 40 can be moved to one of its positions 3-5 to assist this.

The switch 12 is then moved to its second position $S_2$. This produces no change in the vibrator energisation circuit but results in the switch banks 12d and 12e causing the second filter 17 to be produced which transmits signals at 350Hz. These signals are fed through the preset potentiometer $R_{32}$ to the second switch position $S_2$ of the switch bank 12c. The potentiometer $R_{32}$ is pre-set to provide the ratio of 1:8 between the switch positions $S_1$ and $S_2$ which is necessary for the pole scan comparison of output at the two filter frequencies to be made. The wiper of the switch bank 12c is now connected to the input of the meter-amplifier $IC_3$ and the meter responds by either moving to the green side of its scale or the yellow side in accordance with whether the pole being screened passes the test satisfactorily, or is suspect.

If the screening of the pole at the two perpendicular positions used for testing shows the pole to be suspect, the circuitry is moved to its RESOTEST mode. This involves placing the switch 12 into the position $S_3$. The input to the filter circuit is now removed at switch bank 12d and the wiper of the switch bank 40b is connected via the switch position $S_3$ of the switch bank 12c to the switch bank wiper which is permanently connected to the input terminal of the meter-amplifier $IC_3$. In the RESOTEST mode, the switch banks 12a and 12b allow the frequency of oscillation of the multi-vibrator circuit formed by the transistors $TR_1$ and $TR_2$ to be varied by manual control of the potentiometer $RV_1$ and the amplitude of vibration to be controlled by the second manually controllable potentiometer $RV_2$.

Although the equipment used for screening has been described in conjunction with the RESOTEST apparatus, it is to be understood that such equipment may be used completely separately and sold as such. For example, one can construct a simple screening device using the circuit described above by replacing the vibrator side of the circuitry by a simple battery-driven striker mechanism using a miniature electric motor. The output of the transducer 8 may be connected permanently to the filter circuitry provided by the Wien Bridge amplifier, and the three-position switch. Instead of the meter 11 and associated amplification equipment, a very much simpler arrangement using lamps connected to the wiper of the switch bank 12c can be used. A green lamp can be arranged to light if the output of the switch bank 12c at the $S_2$ position falls ones side of the screening ratio 1:8, and a yellow lamp can be arranged to illuminate if it falls the other side to signify that the pole under examination has failed to pass the screening test.

In a modification of the above described equipment, the two switch positions $S_1$ and $S_2$ of the three position switch are fed simultaneously to a comparator which is set with a desired ratio of amplitudes of signals from the two filter circuits. The amplifier is connected to a read-out device which may comprise a meter or lamps and which signifies whether the ratio of the amplitudes of the signals to chosen frequencies which are being simultaneously monitored, are greater or less than the desired ratio of 1:8 necessary for the pole under examination to pass the screening test.

I claim:

1. A method of preliminary screening a wooden pole to see if its characteristics are such that a more thorough examination is called for, comprising injecting into the pole, at a first position, a mechanical signal of constant amplitude obtained from a hammer having a reproducible performance; connecting to a listening point on the other side of the pole an electro mechanical transducer providing an electrical output significant of the level of mechanical vibratory energy present at the listening point; passing the electrical output through two filters having mutually exclusive pass bands, the first filter passing a frequency or range of frequencies found empirically to be virtually unaffected by the condition of the pole and the second filter passing a frequency or range of frequencies whose amplitude is found empirically to be significantly affected by the condition of the pole; comparing the levels of the electrical outputs of the two filters with one another; and providing a read-out value of each electrical output so that, by comparing the read-out values, a decision may be taken on whether the pole should be examined more thoroughly.

2. Apparatus for preliminary screening a wooden pole, comprising a hammer having a reproducible performance and for injecting into the pole a mechanical signal, an electro mechanical transducer providing an electrical output significant of the frequencies and amplitudes of vibratory energy present at a listening point at which the transducer is located on the pole when the apparatus is in use, analysing circuitry connected to receive the electrical output of the transducer and from which is obtained a read-out,
two mutually exclusive pass-band filters in the circuitry arranged to receive the electrical output of the transducer one of the filters passing a first frequency or range of frequencies whose attenuation is found empirically to be unaffected by the condition of the pole, and the other filter passing a frequency or a range of frequencies whose attenuation is found to be significantly affected by the condition of the pole; circuit means in said circuitry and which receives the electrical outputs of the two filters, and, a device in the circuitry which provides the read out from which the poles condition is ascertainable.

3. A method of preliminary screening a wooden pole to see if its characteristics are such that a more thorough examination is called for, comprising injecting into the pole at a first position a mechanical signal of constant amplitude and at a chosen constant frequency; converting mechanical vibratory energy present at a listening point on the other side of the pole into an electrical output; passing the electrical output through two filters sharing a common input terminal and having mutually exclusive pass bands, the first filter passing a frequency or range of frequencies found empirically to be virtually unaffected by the condition of the pole and the second filter passing a frequency or range of frequencies whose amplitude is found empirically to be significantly affected by the condition of the pole; comparing the levels of the electrical outputs of the two filters with one another; and providing a read-out value obtained from the comparison and which signifies with its magnitude whether the pole should be examined more thoroughly.

4. A method claimed in claim 3 in which the ratio of levels of filter outputs marking the transition between an acceptable and an unacceptable pole, is 1:8.

5. The method claimed in claim 3, in which the significantly affected frequency is substantially 350Hz and the virtually unaffected frequency is substantially 100Hz.

6. The method claimed in claim 3 in which the chosen constant frequency of the injected signal is substantially 40Hz.

7. Apparatus for preliminary screening a wooden pole, comprising a vibrator for injecting into the pole a mechanical signal, an electrical circuit determining the frequency of operation of the vibrator and the amplitude of the signal, an electro-magnetic transducer providing an electrical output significant of the frequencies and amplitudes of vibratory energy present at a listening point at which the transducer is located on the pole when the apparatus is in use, analysing circuitry connected to receive the electrical output of the transducer and to supply a read-out value significant of the pole's condition, two band-pass filters in the circuitry arranged to receive the electrical output of the transducer one of the filters passing a first frequency or range of frequencies whose attenuation is found empirically to be virtually unaffected by the condition of the pole, and the other filter passing a frequency or range of frequencies whose attenuation is found to be significantly affected by the condition of the pole, circuit means in said circuitry and which receives the electrical outputs of the two filters, and a read-out device in the circuitry to give a comparative reading of the electrical outputs of the two filters.

8. Apparatus as claimed in claim 7 in which said electrical circuit has first means for varying the frequency and amplitude of operation of the vibrator, and said circuitry has second means operable to by-pass the filters and establish a direct connection between said circuit means of the read-out device and the transducer, whereby the same apparatus is selectively usable for preliminary screening and for a thorough examination of a pole by using the same read-out device which is provided with two scales for this purpose.

9. Apparatus as claimed in claim 8, in which said first means includes a switch having one position at which the vibrator frequency is set at a fixed value with maximum amplification, and another position at which the vibrator frequency is adjustable through a range of frequencies and the amplitude of the vibrators operation is independently controllable.

10. Apparatus as claimed in claim 9, in which the fixed value of the vibrator frequency is substantially 40Hz.

11. Apparatus for preliminary screening a wooden pole comprising a vibrator for injecting into the pole a mechanical signal, an electrical circuit determining the frequency of operation of the vibrator and the amplitude of the signal, an electro-magnetic transducer providing an electrical output significant of the frequencies and amplitudes of vibratory energy present at a listening point at which the transducer is located on the pole when the apparatus is in use, analysing circuitry connected to receive the electrical output of the transducer and to supply a read-out value significant of the pole's condition, two mutually exclusive band-pass filters in the circuitry having Q-factors between 8 and 16 and arranged to receive the electrical output of the transducer one of the filters passing a frequency of 100Hz and the other filter passing a frequency of 350Hz, circuit means in said circuitry and which receives the electrical outputs of the two filters, and a read-out device in the circuitry to give a comparative reading of the electrical outputs of the two filters.

12. Apparatus as claimed in claim 11, in which said one of the filters has a narrow band response peaking at 100Hz with $-3dB$ points at substantially 95Hz and 105Hz and said other filter having a narrow band response peaking at 350Hz with $-3dB$ points at substantially 335Hz and 365Hz, respectively.

13. Apparatus as claimed in claim 12, in which a Wien Bridge amplifier filter provides both filters with appropriate settings of banks of a switch, and a ratio potentiometer is pre-set to provide a desired ratio in the magnitudes of signals transmitted through the Wien Bridge filter at its two frequency settings, respectively.

14. Apparatus as claimed in claim 13, in which the pre-set ratio of the potentiometer is 1:8.

15. Apparatus as claimed in claim 14, in which the read-out device is a centre-reading meter having one side of its scale marked in terms of good wood and the other side calibrated in terms of bad wood.

* * * * *